US 11,337,771 B2

(12) United States Patent
Rizo et al.

(10) Patent No.: US 11,337,771 B2
(45) Date of Patent: May 24, 2022

(54) METHOD AND DEVICE FOR MEASURING THE FLUORESCENCE EMITTED AT THE SURFACE OF BIOLOGICAL TISSUE

(71) Applicant: FLUOPTICS, Grenoble (FR)

(72) Inventors: Philippe Rizo, La Tronche (FR); Marieke Richard, Sassenage (FR); Anthony Daures, Grenoble (FR)

(73) Assignee: FLUOPTICS, Grenoble (FR)

( * ) Notice: Subject to any disclaimer, the term of this patent is extended or adjusted under 35 U.S.C. 154(b) by 517 days.

(21) Appl. No.: 16/478,542

(22) PCT Filed: Jan. 17, 2018

(86) PCT No.: PCT/FR2018/050116
§ 371 (c)(1),
(2) Date: Jul. 17, 2019

(87) PCT Pub. No.: WO2018/134522
PCT Pub. Date: Jul. 26, 2018

(65) Prior Publication Data
US 2019/0328232 A1 Oct. 31, 2019

(30) Foreign Application Priority Data

Jan. 17, 2017 (FR) ...................................... 1750361

(51) Int. Cl.
*A61B 90/00* (2016.01)
*A61B 5/00* (2006.01)
(Continued)

(52) U.S. Cl.
CPC ............ *A61B 90/37* (2016.02); *A61B 5/0071* (2013.01); *A61B 5/0077* (2013.01);
(Continued)

(58) Field of Classification Search
CPC ... A61B 5/0071; A61B 5/0077; A61B 5/6844; A61B 2090/371; A61B 2090/304;
(Continued)

(56) References Cited

U.S. PATENT DOCUMENTS

2009/0103050 A1\* 4/2009 Michaels ............. A61B 3/0075
351/208
2010/0157039 A1 6/2010 Sugai
(Continued)

FOREIGN PATENT DOCUMENTS

EP 1167951 1/2002
EP 2020202 2/2009
(Continued)

*Primary Examiner* — James M Kish
(74) *Attorney, Agent, or Firm* — Occhiuti & Rohlicek LLP (57) ABSTRACT

Measuring fluorescence within a zone on a surface of biological tissue uses a probe that comprises first and second sensors that are constituents of corresponding first and second optical systems and that are fixed relative to each other. The first sensor is configured to detect fluorescent light emitted at said surface and the second sensor detects visible light. The measurement includes projecting a mark onto the zone, and, based on a position of an image of the mark on the second sensor, localizing and locating fluorescence detected by the first sensor in an image of the zone. The image is produced in visible light. The mark is a light mark that is detectable by said second sensor.

17 Claims, 3 Drawing Sheets

(51) Int. Cl.
- *G06T 7/00* (2017.01)
- *H04N 5/225* (2006.01)
- *H04N 5/232* (2006.01)
- *H04N 5/235* (2006.01)

(52) U.S. Cl.
CPC ............ *A61B 5/6844* (2013.01); *A61B 90/39* (2016.02); *A61B 2090/371* (2016.02); *A61B 2090/373* (2016.02); *A61B 2090/3941* (2016.02); *A61B 2560/0223* (2013.01); *A61B 2576/00* (2013.01); *G06T 7/97* (2017.01); *G06T 2207/10004* (2013.01); *G06T 2207/10064* (2013.01); *G06T 2207/30204* (2013.01); *H04N 5/2258* (2013.01); *H04N 5/2354* (2013.01); *H04N 5/23212* (2013.01)

(58) Field of Classification Search
CPC ............ H04N 5/23212; H04N 5/2258; H04N 5/2354; G02B 7/287; G03B 13/20; G06T 7/97
See application file for complete search history.

(56) References Cited

U.S. PATENT DOCUMENTS

| | | | |
|---|---|---|---|
| 2011/0117025 A1* | 5/2011 | Dacosta | A61B 5/445 435/5 |
| 2015/0018690 A1* | 1/2015 | Kang | A61B 1/0638 600/473 |
| 2015/0083932 A1 | 3/2015 | Rizo et al. | |
| 2017/0132774 A1* | 5/2017 | Ruprecht | H04N 5/23299 |
| 2018/0132708 A1 | 5/2018 | Rizo | |
| 2018/0136129 A1 | 5/2018 | Rizo et al. | |
| 2019/0086198 A1* | 3/2019 | Chen | G01B 11/026 |

FOREIGN PATENT DOCUMENTS

| | | | |
|---|---|---|---|
| EP | 2446809 | 5/2012 | |
| FR | 2989876 | 4/2014 | |
| FR | 3036187 | 11/2016 | |
| FR | 3036195 | 11/2019 | |
| JP | 2011-249267 | * 12/2011 | ............ F21S 2/00 |
| WO | WO 2016/011534 | 1/2016 | |
| WO | WO 2016/181076 | 11/2016 | |
| WO | WO2016/181077 | 11/2016 | |

* cited by examiner

METHOD AND DEVICE FOR MEASURING THE FLUORESCENCE EMITTED AT THE SURFACE OF BIOLOGICAL TISSUE

RELATED APPLICATIONS

This application is the national stage of PCT/FR2018/050116, filed on Jan. 17, 2018, which claims the benefit of the Jan. 17, 2017 priority date of French Application No. 1750361, the contents of which are herein incorporated by reference.

FIELD OF INVENTION

The invention relates to medical imaging, and in particular, to measuring fluorescence in biological tissue.

BACKGROUND

It is known to carry out medical imaging using fluorescence of a marker. Such imaging can be useful to evaluate perfusion in biological tissues and to locate zones in such tissues that are in danger of being afflicted by ischemia. Similar forms of imaging are useful for detecting cancerous nodules, for example by using a fluorescent molecular marker, and to assist in excision thereof.

Imaging of this type is also useful for identifying the locations of certain tissues during surgery. For example, parathyroid tissue is embedded in the vicinity of thyroid tissue. Thus, fluorescence provides a way to distinguish between these two very similar tissues during surgery.

In all these cases, it is useful for the fluorescent marker to be detected even at very low concentrations within the biological tissue. It is also useful to localize the marker, and in particular, its distribution and concentration in a field that corresponds to an observed zone of biological tissue.

SUMMARY

In one aspect, the invention features a method for measuring fluorescence in a zone on the surface of a biological tissue.

The method relies in part on a first and second optical systems. The first optical system has a first sensor. This first sensor, which will occasionally be referred to herein as the "fluorescence sensor," detects fluorescence emitted at the surface of the biological tissue. The second optical system comprises a second sensor. This second sensor, which will occasionally be referred to herein as the "optical sensor," detects light in the visible spectrum.

The method described herein includes determining a distance between at least one point of the zone on the surface of the biological tissue and a fixed point in the probe's frame of reference. These will be referred to as the "zonal point" and the "fixed point" respectively.

Using the distance thus determined, the method proceeds to focus the first optical system on this zonal point. It does so in any of a variety of ways, including by using motorized means suitable for moving optical elements such as lenses.

To focus the first optical system on the zonal point, it is necessary to know the distance between this zonal point and the first sensor. However, since this first sensor has a fixed and set position in the probe, it is possible to focus the first optical system simply by knowing any distance between the zonal point and a point whose position is precisely known in the probe's frame of reference.

As used herein, the expressions "distance between a point of the zone on the surface of the biological tissue and a fixed point in the frame of reference of the probe" and "observation distance" designate a distance between the observed biological tissue and a point of the probe the position of which is known, the point of the probe in question possibly then being chosen depending on computational considerations, calibration considerations, and other such considerations.

The methods and systems described herein make it possible to obtain a precise and clear image of the fluorescence on the first sensor. This can be achieved even if the fluorescence emitted in the zone on the surface of the biological tissue to be observed is very low, and possibly insufficient to achieve focus of the first optical system by autofocus based on, for example, image analysis.

The methods and systems described herein also make it possible to obtain a quantitative measurement of the fluorescence that is stable and independent of the distance and orientation of the probe with respect to the biological tissue.

Knowledge of the distance between the zone that is emitting fluorescence and the probe makes it possible to determine, on the basis of the amount of light detected by the fluorescence sensor and the amount of light emitted by the light source associated with the sensor, the amount of light that is being emitted from the biological tissue. As a result, a surgeon has available to him elements that will promote correct interpretation of images. This, in turn, makes it possible for the surgeon to make relevant decisions in real time.

The availability of a means for focusing optical systems over a wide range of distances makes it possible to move the probe. This frees the probe from having to be at a fixed distance from the zone that is to be observed. As a result, the surgeon will have a much easier time manipulating and using the probe.

As a result of the methods and systems described herein, it is also possible to promote the detection of the fluorescence signal by optimizing the dimensions of the fluorescence sensor. In particular, it becomes possible to make the sensor as large as possible while preserving a probe's ability to be manipulated.

The image taken in the visible spectrum provides information on the context and on the topology of the observed zone. Meanwhile, the fluorescence image provides the essential information about the zone.

In most cases, an optical sensor of relatively small size is sufficient to collect the light in the visible spectrum. As a result, it is possible for the probe to be small enough to still be easily manipulated.

In addition, the methods and systems described herein results in a modular probe. This makes it possible to replace the sensor as sensors of higher performance become available on the market and to do so without having to modify the probe's architecture. This is particularly useful because fluorescence sensors have improved rapidly as infrared cameras have improved. This feature thus reduces the likelihood of premature obsolescence.

BRIEF DESCRIPTION OF THE DRAWINGS

Other features and advantages of the invention will become apparent on reading the following detailed description and the appended drawings, in which.

In the figures, the same references have been used to reference elements that are identical or similar.

DETAILED DESCRIPTION

Figure 1:
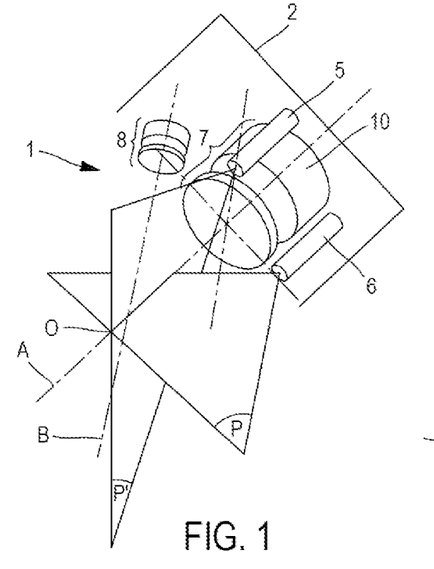
FIG. 1 shows an example of a probe.
Figure 2:
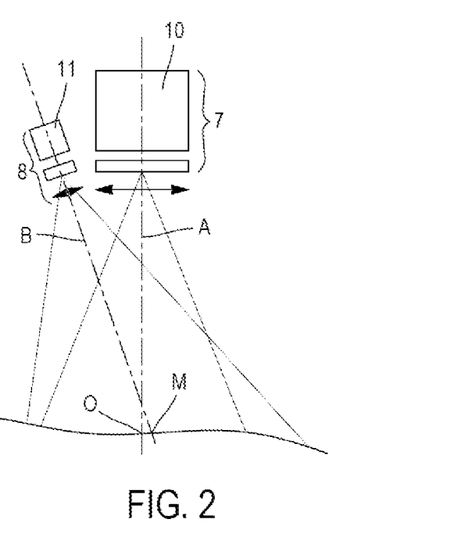
FIG. 2 shows a plane passing through the optical axes of the optical systems of the probe illustrated in FIG. 1.
Figure 3:
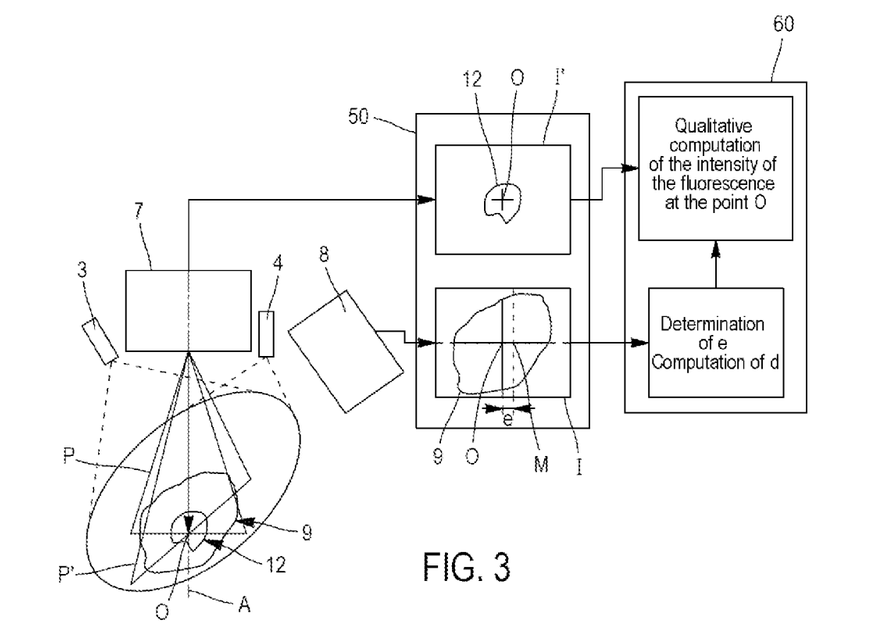
FIG. 3 shows a device according that integrates a probe such as that illustrated in FIGS. 1 and 2.

FIGS. 1-3 show a device that comprises a probe 1 having a casing 2. As can be seen in FIGS. 1 and 2, the casing 2 houses an excitation source 3, a lighting source 4, first and second marking sources 5, 6, and first and second optical systems 7, 8. The excitation source 3 emits excitation radiation.

As shown in FIG. 3, the device also includes a display 50 and a computer 60. The display 50 simultaneously displays a visible image I and a fluorescence image I' of a zone 9 of a biological tissue that is to be observed.

The excitation source 3, which is fixed in the probe's frame of reference, excites at least one fluorescent marker that is located in the zone 9. Meanwhile, the lighting source 4 also illuminates this zone 9.

In many embodiments, the excitation source 3 emits light in the infrared range, and in particular, light having a wavelength of between 630 and 820 nanometers.

Examples of a suitable fluorescent marker include indocyanine green, or "ICG." The excitation spectral band of this marker is between 750 and 820 nanometers. Its fluorescence spectral band is between 800 and 870 nanometers.

The first optical system 7 comprises various optical components, such as focusing lenses and filters. These are organized along a first optical axis A. The first optical system 7 also includes a fluorescence sensor 10, which will also be referred to herein as a "fluorescence-image sensor" or a "first sensor."

The fluorescence sensor 10 includes a photodetector array in which infrared-sensitive photodetectors have been arranged in a matrix. The area of this photodetector array is as large as possible. In some embodiments, the length of the photodetector array's diagonal is larger than one inch. Having a larger area is useful for capturing more photons, thus promoting the fluorescence sensor's sensitivity. On the other hand, it is also important to limit the dimensions of the photodetector array to ensure that the probe 1 does not become so large that it is unwieldy to manipulate. A probe 1 having a front face with a diameter that is less than or equal to eighty millimeters is a good compromise.

The second optical system 8 also comprises various optical components, such as focusing lenses and filters. These are organized along a second optical axis B. The second optical system 8 also has an image sensor 11 that is sensitive in the visible spectrum. This image sensor 11 is likewise an array of photodetectors that has been arranged in a matrix.

The image sensor 11, which will also be referred to herein as the "optical sensor" or "second sensor," can be implemented by a charge-coupled device (CCD) or by a complementary metal-oxide semiconductor (CMOS) device. Since the supply of visible light is expected to be far more copious than that of infrared light, the photodetector is chosen to have the smallest possible area consistent with preserving good image quality given the available visible light. In some embodiments, the length of its diagonal is less than half an inch. In others, it is less than even a third of an inch.

In order to simplify the computations of the distances mentioned below, it is preferable for the first and the second optical axes A, B to cross. They are then found in the same plane P of space.

In some embodiments, the image sensor 11 allows observation of a color image of the zone 9. However, there also exist embodiments in which the image sensor 11 obtains a black-and-white or gray scale image of the zone 9.

In yet other embodiments, the image sensor 11 and the fluorescence sensor 10 share the same optical axis, for example as a result of an angular redirection. In some cases, the sensors are implemented with a single sensor and a modified Bayer filter and a rangefinder placed on the probe 1 and based on a computation of the time-of-flight or a triangulation. But, in this case, the back focus is thus increased, while it is desired to work with the largest possible optical aperture.

In some implementations, the first and second marking sources 5, 6 are laser sources that emit green light. In others, the first and second marking sources 5, 6 radiate with a wavelength of between 520 and 532 nanometers. As a result, Thus, the wavelength emitted by the marking sources 5, 6 is visible by the image sensor 11 but not by the fluorescence sensor 10. In addition, the first and second marking sources 5, 6 do not excite fluorescence that would be detected by the fluorescence sensor 10.

The first and second marking sources 5, 6 each illuminate a plane P' or P of space. For simplicity's sake, "plane" does not refer to an infinite two-dimensional surface but instead refers to a sector located in such a plane P, P'.

The plane P projected by the second marking source 6 corresponds to the spatial plane in which lie the first and second optical axes A, B. The plane P' projected by the first marking source 5 then corresponds to a plane perpendicular to that in which the first and second optical axes A, B are found and the plane P. The intersection of the two planes P, P' projected by the first and second marking sources 5, 6 therefore corresponds to the first optical axis A.

The intersection of the two planes P, P' is projected onto a point O, in the zone 9. This point O is placed on the optical axis of the first optical system A. It is fixed for the fluorescence sensor 10, whatever the orientation and position of the probe 1 with respect to this zone 9 might be. In contrast, the point O moves with the optical sensor 11 upon movement of the probe 1.

The projection of the second optical axis B onto the zone 9 corresponds to a point M. This point M is fixed for the optical sensor 11. The optical sensor 11 determines the position of this point M within the image I. Its position is therefore known by construction.

The position of the point O, as seen by the optical sensor 11 relative to the position of the point M, as seen by the optical sensor 11, corresponds to a distance e. This distance e, varies depending on the distance between the point O and a fixed point in the probe's frame of reference. As a result, the distance e makes it possible to determine the distance between the optical sensor 11 and the surface onto which this movable point O has been projected. Since the image sensor 11 and the fluorescence sensors 10 are fixed with respect to each other, the determination, by the computer 60, of this distance e also provides knowledge of the distance between the fluorescence sensor 10 and the point O on the surface of the zone 9.

Knowledge of the distance between the fluorescence sensor 10 and the surface of the zone 9 enables certain useful steps to be carried out.

First of all, such knowledge permits calculation of how much amount excitation light the biological tissue 9 receives.

Secondly, such knowledge permits adjustment of the focus of the first optical system 7 on the surface of the zone 9.

Finally, such knowledge promotes safer use of the probe 1. It does so by automatically reducing the emission of the excitation source 3 whenever the surgeon holds the probe 3 so close to the zone's surface that there exists a significant risk of actually overheating this tissue. Availability of such knowledge thus permits having a variable-intensity excitation source 3 that adaptively controls its output as a function of distance between at least one point of the zone 9 and the fixed point in the probe's frame of reference of the probe is provided.

Furthermore, the position of the point O appears in the image I. The point O marks the intersection of the planes P and P' projected onto the surface so as to be visible by the optical sensor 11. This position corresponds to the projection of the first optical axis A onto the zone 9.

Knowing the position of the point O allows one to pinpoint, in the image I, the central point of the image I' as shown in FIG. 3. Since the light mark at the point O appears in the image captured by the optical sensor 11, it becomes possible to localize and locate the fluorescence detected by the fluorescence sensor within an image of the zone 9 as seen in visible light.

The foregoing ability to localize the fluorescence becomes particularly advantageous in those configurations in which the casing 2 houses two sensors side-by-side. In such configurations, the two sensors would each capture corresponding images I, I'. These images I, I' are of different fields that are observed from different angles. The images I, I' acquired by the optical and fluorescence sensors 11, 10 would then be displayed, one beside the other. However, a surgeon could still easily locate, using the point O in the image I formed using the optical sensor 11, the position and orientation of the fluorescent area 12 that he is able to observe in the image I' acquired by the fluorescence sensor 10.

Figure 4:
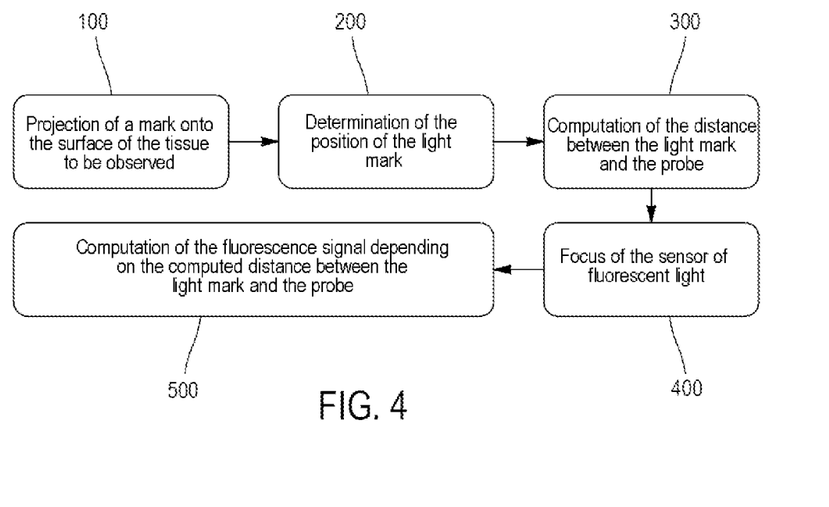
FIG. 4 shows various steps of a method.

FIG. 4 shows an example of one implementation of the foregoing device.

The implementation begins with having the excitation source 3, the lighting source 4, and the two marking sources 5, 6 illuminate the zone 9 that is to be observed (step 100).

Next, an image processing algorithm determines, in real time, the position O within the field detected by the optical sensor. This position O is that of the cross that is formed by the intersection of the two planes P, P' projected by the marking sources 5, 6 (step 200).

With the cross's position now having been determined, the method continues with calculating the distance between a fixed point in the probe's frame of reference and the zone's surface (step 300), verifying that this distance will be sufficient to guarantee that the excitation source 3 does heat the tissue being observed to an extent that would create undue risk, and focusing the first optical system 7 onto the surface (step 400), all of which are carried out in real time.

The intensity of the fluorescence signal is then computed depending on the distance computed beforehand between a fixed point in the probe's reference frame and the zone's surface (step 500).

A suitable method for determining the position of the point O within the image I captured by the optical sensor 11 is to adaptively threshold colorimetric components. A suitable method for determining the distance between the fixed point in the probe's frame of reference and the zone's surface is to use a conventional range-finding method or to use a prior calibration of the probe 1 that gives the distance between a fixed point in the probe's reference frame and the zone's surface depending on the movement of the cross in the image I captured by the optical sensor 11. A suitable such fixed point would be a porthole of the probe 1.

Other methods can be used to determine the distance between the fluorescence sensor 10 and the zone's surface. Among these are methods that do not rely on image-analysis. For example, some embodiments feature determining this distance by using the time-of-flight method described in FR3036195A1, the contents of which are herein incorporated by reference.

The process of determining the fluorescence signal's intensity as a function of the distance between the fluorescence sensor 10 and the zone's surface relies on the recognition that, for a constant exposure time, the fluorescence signal depends directly on the excitation irradiance received by the biological tissue at the zone 9. However, for a constant excitation power, when the excitation source 3 is on the probe 1, this irradiance varies with the distance between the zone 9 and the excitation source 3. Therefore, since this distance is known in real time, it is possible to normalize the value of the intensity of the measured fluorescence with respect to this distance.

Specifically, the irradiance received by a zone 9 is inversely proportional to the square of the distance that separates it from the excitation source 3. However, the intensity of the fluorescence signal emitted by the zone 9 is also proportional to the amount of excitation light reaching the zone 9 per unit of time. Therefore, the intensity of the fluorescence signal detected is also inversely proportionally to the square of the distance d separating the fluorescence-emitting zone 12 from the excitation source 3:

$$\text{Fluorescence signal } (d) = A \cdot \frac{1}{d^2}$$

where A is a coefficient that takes into account the excitation power of the excitation source 3, the absorption and emission properties of the biological tissue being observed, the sensitivity of the fluorescence sensor 10 in the wavelength range of the fluorescent emission, and the concentration of the fluorophore per unit area of the biological tissue that is being observed.

Within the probe 1, the excitation source 3 and the fluorescence sensor 10 are fixed with respect to each other. Therefore, the ratio of the intensities of the fluorescence signals measured respectively at two distances $d_1$ and $d_2$ depends only on these distances:

$$\frac{\text{Fluorescence signal } (d_1)}{\text{Fluorescence signal } (d_2)} = \frac{d_2^2}{d_1^2}$$

For the surgeon to be able to observe an image in which the intensity of the fluorescence signal does not depend on the distance at which he places the probe 1 relative to the zone 9, the displayed fluorescence image I' is corrected, in real time, depending on this distance.

A procedure for carrying out such a correction begins with a first step that includes measuring the intensity for each pixel in an image captured by the fluorescence sensor 10. In a second step, the optical sensor 11 measures the distance between the excitation source 3 and the zone 9. A third step that follows corrects the intensities determined in the first step for each pixel. This correction includes choosing an arbitrary distance $d_{ref}$ and basing the correction in part on that distance. A fourth step includes displaying an image that results from having corrected the intensities in the third step.

To ease the computational burden, it is useful to assume that that the image I' is on a planar surface. Any error introduced by this assumption has proven to be negligible.

Figure 5:
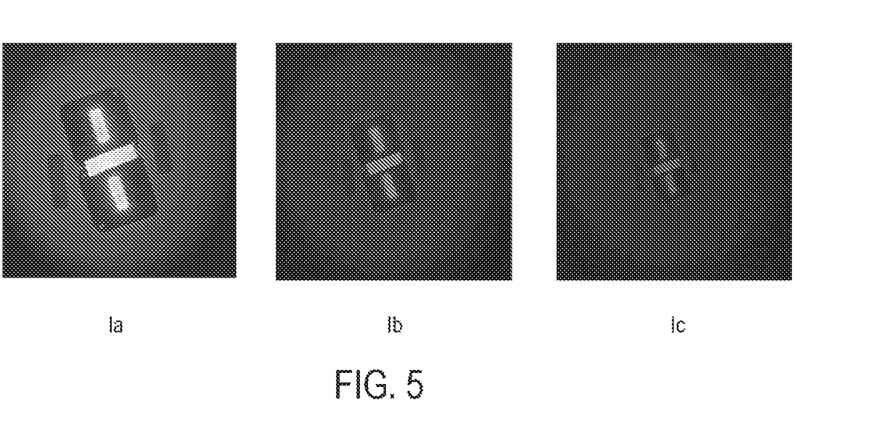
FIGS. 5 and 6 show fluorescence images obtained using the probe of the illustrated in FIGS. 1 and 2.

FIG. 5 shows first, second, and third images Ia, Ib, Ic that have yet to be corrected.

The first image Ia is that of a scene containing emitters 13 of a fluorescence signal. The first image Ia does not actually correspond to any zone 9. It was chosen for instructional purposes because of the ease with which a corresponding scene could be obtained. However, the explanation that follows is agnostic to the content of an image.

The first image Ia was produced from the fluorescence signal detected by the fluorescence sensor 10 with the probe 1 having been placed 115 millimeters from the emitters 13 of the fluorescence signal.

The second image Ib shows the same scene but with the probe 1 having been repositioned to be further from the emitters 13. In the second image Ib, the probe is now 190 millimeters from the emitters 13.

The third image Ic shows the same scene but with the probe 1 now having been placed 262 millimeters from the emitters 13.

It is apparent from comparing the images that the farther the probe 1 is from the scene containing the emitters 13 of the fluorescence signal, the lower the intensity of the fluorescence signal appears. This is because moving the probe away also moves the excitation source 3 away. As indicated above, the intensity of the detected fluorescence signal is inversely proportional to the square of the distance d that separates the fluorescence-emitting zone from the excitation source 3.

The table below gives the values of the intensity of the fluorescence, quantified in grayscale, as a function of the distance between the probe 1 and the emitters 13:

| Distance (millimeters) | Grayscale |
|---|---|
| 115 | 45651 |
| 132 | 35738 |
| 163 | 24177 |
| 190 | 18325 |
| 235 | 12208 |
| 262 | 9894 |
| 295 | 7881 |

The foregoing measurements of the values of the intensity of the fluorescence were all taken in the same region of interest. For example, for the images of FIGS. 5 and 6, the region of interest corresponds to the central rectangle.

In contrast, if it is desired to display an image the intensity of the fluorescence of which as seen by an operator is independent of the distance between the probe 1 and the zone 9 of biological tissue to be observed, or observation distance di, the ratio of the intensity of the fluorescence signal for various observation distances di to the intensity of the fluorescence signal for an arbitrarily chosen reference distance $d_{ref}$, for example equal to 163 millimeters, is computed:

$$\frac{\text{Fluorescence signal }(d_1)}{\text{Fluorescence signal }(d_{ref})}\text{(crosses) and }\frac{d_{ref}^2}{d_1^2}\text{(circles),}$$

where $d_{ref}$ is equal to 163 millimeters.

The error $$\frac{\frac{\text{Fluorescence signal }(d_1)}{\text{Fluorescence signal }(d_{ref})} - \frac{d_{ref}^2}{d_1^2}}{\frac{\text{Fluorescence signal }(d_1)}{\text{Fluorescence signal }(d_{ref})}}$$

is also computed.

Results obtained for a plurality of observation distances di are given in the table below:

| Distances di (millimeters) | Grayscale | Fi/Fref | dref²/di² | Error in the interpolation |
|---|---|---|---|---|
| 115 | 45651 | 1.89 | 2.01 | 6.4% |
| 132 | 35738 | 1.48 | 1.52 | 3.2% |
| 163 | 24177 | 1.00 | 1.00 | 0.0% |
| 190 | 18325 | 0.76 | 0.74 | 2.9% |
| 235 | 12208 | 0.50 | 0.48 | 4.7% |
| 262 | 9894 | 0.41 | 0.39 | 5.4% |
| 295 | 7881 | 0.33 | 0.31 | 6.3% |

Figure 7:
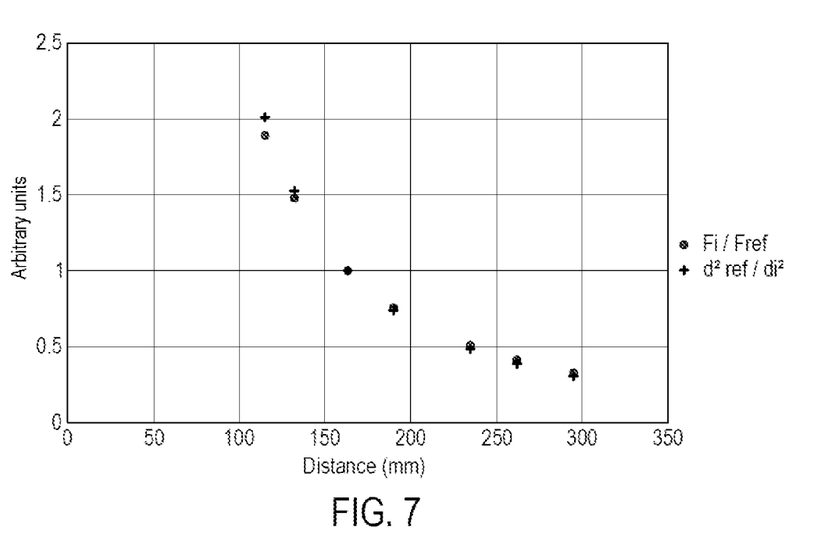
FIG. 7 is a graph illustrating the variation, as a function of observation distance, of the fluorescence-intensity ratio calculated on the basis of measurements carried out with a device such as that illustrated in FIG. 3, and the variation, as a function of observation distance, of a ratio of the square of the observation distances.

The values given in the foregoing table represent ratios of the fluorescence intensities and ratios of the square of the observation distances di as a function of the observation distance $d_i$. It is apparent from plotting these values, as shown in FIG. 7, that the curve of $$\frac{d_{ref}^2}{d_1^2}$$

follows the same tendency as the curve of $$\frac{\text{Fluorescence signal }(d_1)}{\text{Fluorescence signal }(d_{ref})}.$$

Furthermore, the error between these two ratios is sufficiently small for it to be possible to compute, with an acceptable degree of error, namely an error of less than 10%, the value of the intensity of the fluorescence using the ratio of the square of the observation distances.

Figure 6:
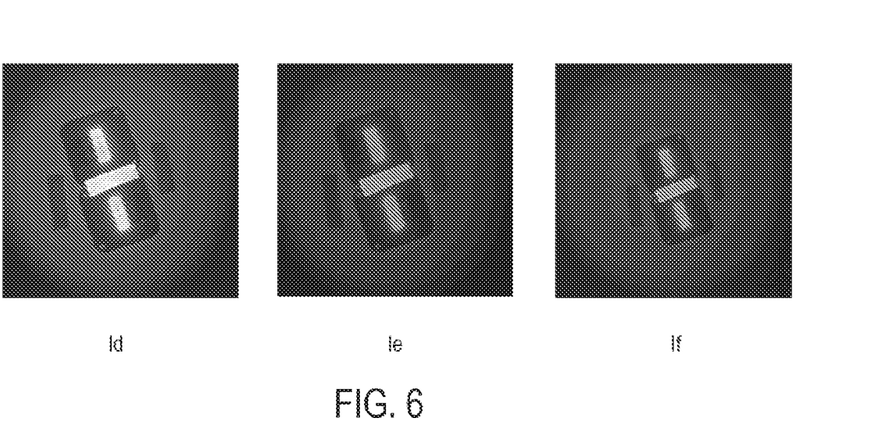

FIG. 6 shows a fourth image Id, which corresponds to the fluorescence-signal emitters 13 observed with the probe 1 at an observation distance of 115 millimeters. A fifth image If in FIG. 6 corresponds to the same fluorescence-signal emitters 13 observed with the probe 1 at an observation distance di equal to 163 millimeters. A sixth image Ie corresponds to the fourth image Id taken at an observation distance of 115 millimeters, but corrected as indicated above using, as a reference, the fluorescence signal obtained at a reference distance dref that was equal to 163 millimeters.

By thus correcting the intensity of the fluorescence detected as a function observation distance di, it is possible to display, in real time, a signal having an intensity level that is independent of this distance and of the orientation of the probe 1. More generally, the method makes it possible to modulate, on the display, the intensity of the signal associated with the detected fluorescence and to do so as a function of the distance determined between at least one point of the zone 9 and the probe 1.

In addition to providing real-time display, it is also possible to provide the surgeon with quantitative information in real time. Knowledge of the level of fluorescence of a tissue during an operation may be very useful. For example, this knowledge may allow the level of perfusion of a biological tissue to be evaluated.

As indicated above, the device according to the invention may comprise two laser marking sources that allow a targeted cross to be formed. It is then possible to detect the fluorescence signal at the center of this cross in order to obtain a quantitative value of the signal: Fluorescence signal $(d_{ref}, t_{ref})$, for a reference distance $d_{ref}$ and a reference exposure time $t_{ref}$.

Thus, on the basis of a value of the fluorescence signal detected under particular conditions of use (at a distance $d_i$ and for an exposure time $t_i$), it is possible to calculate the value that the intensity of the fluorescence signal would have Fluorescence signal $(d_i^{ref}, t_i^{ref})$ under reference conditions $(d_{ref}, t_{ref})$:

$$\text{Fluorescence signal}\left(d_i^{ref}, t_i^{ref}\right) = \frac{t_{ref}}{t_i} \cdot \frac{d_i^2}{d_{ref}^2} \cdot \text{Fluorescence signal}(d_i, t_i)$$

Thus, the surgeon is provided with quantitative information that is stable, whatever the orientation of the probe 1 and the distance that separates the excitation source 3, from the zone 9 of the biological tissue to be observed, and independent of exposure time.

The invention claimed is:

1. A method of localizing fluorescence within a zone on a surface of biological tissue using a probe that comprises a first optical system having a first sensor configured to detect fluorescent light, a second optical system having a second sensor configured to detect visible light, and a marking-light source, wherein said first sensor is fixed relative to said second sensor such that an optical axis of said first optical system is not coaxial with an optical axis of said second optical system, wherein localizing said fluorescence comprises projecting a mark onto said zone at a center of said first optical system with said marking-light source, and, based on a position of said mark in a visible image of said zone acquired by said second sensor, localizing fluorescence within said zone by simultaneously displaying said visible image and a fluorescence image acquired by said first sensor.

2. The method of claim 1, further comprising placing said mark along the optical axis of said first optical system.

3. The method of claim 1, further comprising, using a position of said mark in said visible image, determining a distance between a first point and a second point in said zone and using said distance to focus said first optical system onto said first point, wherein said second point is a fixed point in a frame of reference of said probe.

4. The method of claim 3, wherein determining said distance between said first and second points comprises determining said distance based at least in part on a displacement of said mark in said visible image, wherein said displacement is a displacement of said probe relative to said zone.

5. The method of claim 3, further comprising modulating a fluorescence signal that is detected by said first sensor, wherein modulating comprises modulating based on said distance.

6. The method of claim 3, wherein said probe further comprises an excitation light source and controlling an intensity of light emitted by said excitation light source based on said distance.

7. An apparatus for measuring fluorescence in a zone on a surface of biological tissue, said apparatus comprising:
a marking-light source configured to project a light mark onto said surface;
a probe comprising
a first optical system having a first sensor configured to detect fluorescence emitted from said surface;
a second optical system having a second sensor configured to detect visible light;
wherein said first sensor is fixed relative to said second sensor such that an optical axis of said first optical system is not coaxial with an optical axis of said second optical system;
wherein said light mark is detectable by said second sensor and undetectable by said first sensor, wherein said light mark is coaxial with said optical axis of said first optical system.

8. The apparatus of claim 7, wherein said marking-light source is fixed relative to said first and second sensors.

9. The apparatus of claim 7, wherein the optical axes of said first and second optical systems are coplanar.

10. The apparatus of claim 7, wherein said marking-light source is a first marking-light source, wherein said apparatus further comprises a second marking-light source, wherein each of said first and second marking-light sources comprises a laser emitter that emits corresponding first and second planar light beams having a wavelength that is detectable by said second sensor and undetectable by said first sensor, wherein one of said beams passes through said first and second optical axes, wherein, as a result of said beams being perpendicular, said mark is a cross that corresponds to an intersection of said beams, and wherein said cross is projected onto said surface and centered on an optical axis of said first optical system.

11. The apparatus of claim 7, further comprising means for determining a distance between a first point and a second point and means for focusing said first optical system on said first point using said distance, wherein said first point is a point on said zone and wherein said second point is a fixed point in a frame of reference of said probe.

12. The apparatus of claim 11, wherein said means for determining a distance determines said distance without performing image analysis on images acquired by said first and second sensors.

13. The apparatus of claim 11, wherein said distance is determined based at least in part on a displacement of said mark in an image taken by said second sensor and displacement of said probe relative to said zone.

14. The apparatus of claim 7, wherein said first and second sensors have corresponding first and second detecting areas that differ from each other.

15. The apparatus of claim 14, wherein said first detecting area is at least twice as large as said second detecting area.

16. The apparatus of claim 15, wherein said first sensor has a dimension that is larger than an inch and said second sensor has a corresponding dimension that is smaller than half an inch.

17. The apparatus of claim 7, further comprising an excitation light source that is fixed relative to said first and second sensors.

* * * * *